United States Patent [19]

Goto et al.

[11] 4,421,693
[45] Dec. 20, 1983

[54] AMINOSULFENYL CHLORIDE DERIVATIVES

[75] Inventors: Takeshi Goto; Takashi Soeda; Nobuyoshi Asai; Akira Tanaka, all of Tokushima, Japan

[73] Assignee: Otsuka Chemical Co., Ltd., Osaka, Japan

[21] Appl. No.: 361,931

[22] Filed: Mar. 25, 1982

[30] Foreign Application Priority Data

Mar. 30, 1981 [JP] Japan .................................. 56-47785
May 22, 1981 [JP] Japan .................................. 56-78529
Nov. 5, 1981 [JP] Japan .................................. 56-177928
Nov. 5, 1981 [JP] Japan .................................. 56-177929

[51] Int. Cl.$^3$ .......................................... C07C 161/00
[52] U.S. Cl. ................................ 260/464; 260/465 D; 260/465 E; 260/465.4; 260/465.5 R; 560/16; 560/121; 560/123; 560/124; 560/125; 560/137; 560/147; 560/150; 549/470
[58] Field of Search ............... 560/16, 147, 137, 150, 560/121, 123, 124, 125; 260/465 D, 465 E, 465.4, 464, 465.5 R

[56] References Cited

U.S. PATENT DOCUMENTS 2,649,470 8/1953 Harman .................. 260/465.5 R
2,766,236 10/1956 Harman .................. 260/465.5 R

*Primary Examiner*—Richard Raymond
*Assistant Examiner*—Bernard Dentz

*Attorney, Agent, or Firm*—Sughrue, Mion, Zinn, Macpeak & Seas

[57] ABSTRACT

An aminosulfenyl chloride derivative represented by the formula (I):

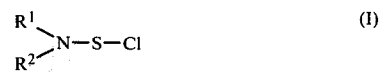

wherein $R^1$ and $R^2$ are defined in the specification, which is useful as an intermediate for the preparation of a carbamate derivative represented by the formula (III):

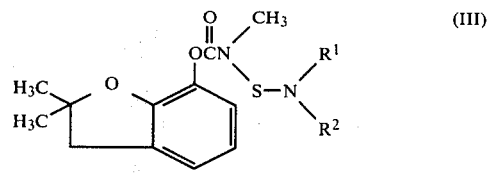

wherein $R^1$ and $R^2$ are the same as defined above, the carbamate derivative having an insecticidal, miticidal or nematocidal activity, is disclosed. A process for preparing the aminosulfenyl chloride of the formula (I), and a process for preparing the carbamate derivative of the formula (III) using the aminosulfenyl chloride of the formula (I) are also disclosed.

1 Claim, No Drawings

AMINOSULFENYL CHLORIDE DERIVATIVES

This invention relates to a novel aminosulfenyl chloride derivative which is useful as an intermediate for the preparation of a carbamate derivative having an insecticidal, miticidal or nematocidal activity, and to a process for preparing the aminosulfenyl chloride derivative. The invention further relates to a process for preparing the carbamate derivative using as a starting material the aminosulfenyl derivative. In the present specification, the term "insecticidal" includes "miticidal" and "nematocidal" in addition to "insecticidal", and the term "insect(s)" includes "mite(s)" and "nematode(s)" in addition to "insect(s)", respectively, unless otherwise indicated.

An aminosulfenyl chloride derivative according to this invention is expressed by the formula (I):

wherein $R^1$ and $R^2$, which may be the same or different, each represents (1) —X—COOR$^3$, in which X represents an alkylene group having 1 to 6 carbon atoms, and $R^3$ represents an alkyl group having 1 to 8 carbon atoms or a cycloalkyl group having 3 to 6 carbon atoms; or (2) —Y—CN, in which Y represents an alkylene group having 1 to 6 carbon atoms; and $R^2$ further represents an alkyl group having 1 to 8 carbon atoms; a cycloalkyl group having 3 to 6 carbon atoms; a benzyl group which may be substituted with a halogen atom, an alkyl group having 1 to 3 carbon atoms or an alkoxy group having 1 to 3 carbon atoms; a phenyl group which may be substituted with a halogen atom, an alkyl group having 1 to 3 carbon atoms or an alkoxy group having 1 to 3 carbon atoms; or —Z—R$^4$, in which Z represents a carbonyl group or a sulfonyl group, and $R^4$ represents an alkyl group having 1 to 6 carbon atoms, a phenyl group which may be substituted with an alkyl group having 1 to 3 carbon atoms or a halogen atoms, an alkoxy group having 1 to 3 carbon atoms or a phenoxy group, which has not been disclosed in any literature and which has been discovered by the present inventors for the first time.

In the definition for the formula (I) above, the alkyl moiety in the alkyl group, alkylene group and alkoxy group may be straight chain or branched chain.

The compound of the formula (I) is highly reactive and can easily react with a group such as an —NH$_2$ group, an —SH group, an —OH group, etc., and therefore, it is useful as an intermediate for various reactions. For example, the compound of the formula (I) can be reacted with 2,3-dihydro-2,2-dimethylbenzofuran-7-yl N-methyl-carbamate (hereinafter referred to as "carbofuran", as generally called) represented by the formula (II):

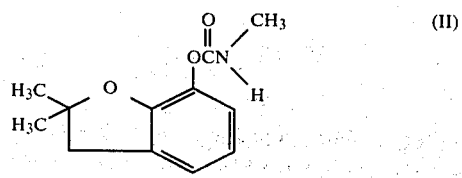

to introduce into a 2,3-dihydro-2,2-dimethylbenzofuran-7-yl N-(N,N-disubstituted aminosulfenyl)-N-methylcarbamate represented by the formula (III):

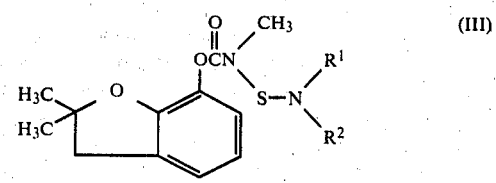

wherein $R^1$ and $R^2$ are the same defined above, which is useful as an insecticide.

Carbofuran per se is known to have the highest insecticidal activity heretofore known in the known carbamate compounds, but it causes problems in practical use due to high toxicity to warm-blooded animals. On the other hand, the compound of the formula (III) is comparable to carbofuran in insecticidal activity or controlling effect on agricultural and forestry noxious insects and household noxious insects, with the toxicity to warm-blooded animals being as low as about 1/5 to about 1/100 the toxicity of carbofuran. Accordingly, the compound of the formula (I) is quite useful as an intermediate in the preparation of insecticides.

The compound of the formula (I) can be prepared by various methods, and above all, the following Methods 1 and 2 are preferred.

Method 1

The compound of the formula (I) is easily obtainable by the reaction of an amine derivative represented by the formula (IV):

wherein $R^1$ and $R^2$ are the same as defined above, with sulfur monochloride or sulfur dichloride as illustrated in the following reaction (1) or (2).

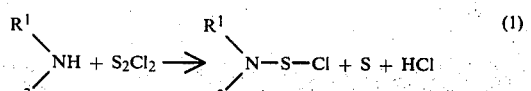

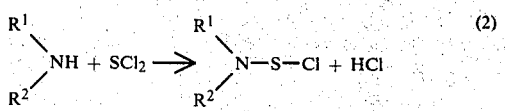

In the above reactions (1) and (2), $R^1$ and $R^2$ are the same as defined above.

In any of the reaction (1) wherein sulfur monochloride is used and the reaction (2) wherein sulfur dichloride is used, the reaction can proceed within a short period of time, but in the reaction (1), sulfur is liberated. The reaction in both the reactions (1) and (2) proceeds under the same condition, and may be conducted in the presence or absence of a solvent. Examples of the solvent which can be used include halogenated hydrocarbons such as methylene chloride, chloroform, carbon tetrachloride, dichloroethane, trichloroethylene, methylchloroform, etc.; ethers such as diethyl ether, dipropyl ether, dibutyl ether, tetrahydrofuran, dioxane, etc.; hydrocarbons such as n-pentane, n-hexane, n-heptane, cyclohexane, etc.; and aromatic hydrocarbons such as benzene, toluene, xylene, chlorobenzene, etc. The proportion of the compound of the formula (IV) and sulfur monochloride or sulfur dichloride is not particularly limited but is widely variable suitably. Usually 1 to 2 moles, preferably 1 to 1.2 moles, of the latter is used per mole of the former. Preferably, the reaction is carried out in the presence of a basic compound. Examples of the basic compound which can be used include tertiary amines such as triethylamine, tributylamine, dimethylaniline, diethylaniline, ethylmorpholine, etc.; and pyridines such as pyridine, picoline, lutidine, etc. The basic compound can be used in an amount sufficient to capture the hydrogen chloride to be produced by the reaction as a by-product. Usually, about 1 to about 2 moles, preferably 1 to 1.5 moles, of the basic compound is used per mole of the compound of the formula (IV). The reaction, which proceeds with cooling, at room temperature or with heating, is carried out usually at about $-20°$ to about 50° C., preferably $-10°$ to 30° C. The reaction time varies depending upon the basic compound used, but usually is about 1 to about 2 hours.

Method 2

The compound of the formula (I) is easily obtainable by reacting the compound of the formula (IV) and sulfur monochloride to form a bisaminodisulfide derivative represented by the formula (V):

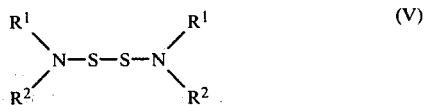

wherein $R^1$ and $R^2$ are the same as defined above, and then chlorinating it as illustrated in the following reactions (3) and (4).

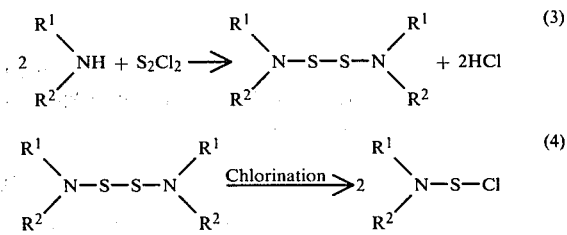

The reaction in the reaction (3) may be conducted in the presence or absence of a solvent, or by a two-phase reaction of a solvent and water. Examples of the solvent which can be used include halogenated hydrocarbons such as methylene chloride, chloroform, carbon tetrachloride, dichloroethane, trichloroethylene, methylchloroform, etc.; ethers such as diethyl ether, dipropyl ether, dibutyl ether, tetrahydrofuran, dioxane, etc.; hydrocarbons such as n-pentane, n-hexane, n-heptane, cyclohexane, etc.; and aromatic hydrocarbons such as benzene, toluene, xylene, chlorobenzene, etc. In the reaction (3), the proportion of the compound of the formula (IV) and sulfur monochloride is not particularly limited but is widely variable suitably. Usually, about 0.5 mole of the latter is used per mole of the former. Preferably, the reaction in the reaction (3) is carried out in the presence of a basic compound. The amine compound used as a starting material in the reaction (3) can be used as the basic compound. Other examples of the basic compound include tertiary amines such as triethylamine, tributylamine, dimethylaniline, diethylaniline, ethylmorpholine, etc.; and pyridines such as pyridine, picoline, lutidine, etc. On the other hand, when the reaction is carried out by the two-phase reaction of a solvent and water, sodium hydroxide, potassium hydroxide, sodium carbonate, potassium carbonate, etc., can be used as the basic compound. The basic compound can be used in an amount sufficient to capture the hydrogen chloride to be produced by the reaction as a by-product. Usually, about 1 to about 10 moles, preferably 1 to 5 moles, of the basic compound is used per mole of the compound of the formula (IV). The reaction, which proceeds with cooling, at room temperature or with heating, is carried out usually at about $-20°$ to about 50° C., preferably $-10°$ to 30° C. The reaction time varies depending upon the basic compound used, but usually is about 1 to about 2 hours. The thus obtained bisaminodisulfide derivative of the formula (V) can be purified and then used, or the reaction solution can be washed with water, dried and then used in the sequent reaction as it is.

The reaction in the reaction (4) may be conducted in the presence or absence of a solvent. Any of the solvents which are useful in the reaction (3) can be used. Examples of a chlorinating agent which can be used include chlorine, sulfuryl chloride, etc. The proportion of the compound of the formula (V) and the chlorinating agent is not particularly limited but is widely variable suitably. Usually, about 0.5 to about 5 moles, preferably 0.5 to 1.5 moles, of the latter is used per mole of the former. The reaction, which proceeds with cooling, at room temperature or with heating, is carried out usually at about $-20°$ to about 50° C., preferably $-10°$ to 30° C. The reaction completes within about one to about 2 hours.

The amine compounds of the formula (IV) are known compounds.

Examples of useful amine compounds of the formula (IV) are those secondary amines represented by the formulae (VI) to (X):

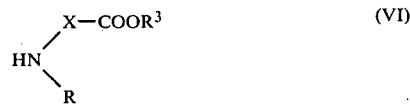

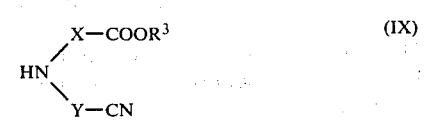

In the formulae (VI) to (X), X, Y and $R^3$ are as defined above; R represents an alkyl group having 1 to 8 carbon atoms; a cycloalkyl group having 3 to 6 carbon atoms;

a benzyl group which may be substituted with a halogen atom, an alkyl group having 1 to 3 carbon atoms or an alkoxy group having 1 to 3 carbon atoms; a phenyl group which may be substituted with a halogen atom, an alkyl group having 1 to 3 carbon atoms or an alkoxy group having 1 to 3 carbon atoms; or Z'-R$^{4'}$, in which Z' represents a carbonyl group or a sulfonyl group, and R$^{4'}$ represents an alkyl group having 1 to 6 carbon atoms, a phenyl group, a benzyl group, an alkoxy group having 1 to 6 carbon atoms or a phenoxy group (in which the alkyl group and alkoxy group may be straight or branched chain); R$^{3''}$ has the same meaning as in R$^3$; X'' has the same meaning as in X; and Y'' has the same meaning as in Y.

Representative examples of the amine compound of the formula (VI) are N-methylglycine methyl ester, N-methylglycine ethyl ester, N-methylglycine butyl ester, N-ethylglycine ethyl ester, N-n-propylglycine ethyl ester, N-isopropylglycine ethyl ester, N-n-butylglycine ethyl ester, N-isobutylglycine ethyl ester, N-sec-butylglycine ethyl ester, N-n-octylglycine ethyl ester, N-cyclohexylglycine ethyl ester, N-benzylglycine ethyl ester, N-(4-methylbenzyl)glycine ethyl ester, N-(4-chlorobenzyl)glycine ethyl ester, N-phenylglycine ethyl ester, N-(3-methylphenyl)glycine ethyl ester, N-(4-methoxyphenyl)glycine ethyl ester, N-methoxycarbonylglycine ethyl ester, N-ethoxycarbonylglycine methyl ester, N-ethoxycarbonylglycine ethyl ester, N-ethoxycarbonylglycine phenyl ester, N-phenoxycarbonylglycine ethyl ester, ethyl N-methylaminopropionate, ethyl N-n-propylaminopropionate, methyl N-isopropylaminopropionate, ethyl N-isopropylaminopropionate, butyl N-isopropylaminopropionate, 2-ethylhexyl N-isopropylaminopropionate, methyl N-n-butylaminopropionate, ethyl N-n-butylaminopropionate, ethyl N-isobutylaminopropionate, ethyl N-sec-butylaminopropionate, ethyl N-t-butylaminopropionate, ethyl N-n-amylaminopropionate, ethyl N-isoamylaminopropionate, ethyl N-n-hexylaminopropionate, ethyl N-cyclohexylaminopropionate, ethyl N-ethoxycarbonylaminopropionate, N-acetylglycine ethyl ester, N-chloroacetylglycine ethyl ester, N-propionylglycine ethyl ester, N-benzoylglycine ethyl ester, N-(4-chlorobenzoyl)glycine ethyl ester, N-tosylglycine ethyl ester, etc.

Representative examples of the amine compound of the formula (VII) are N-methylaminoacetonitrile, N-ethylaminoacetonitrile, N-n-propylaminoacetonitrile, N-isopropylaminoacetonitrile, N-n-butylaminoacetonitrile, N-isobutylaminoacetonitrile, N-benzylaminoacetonitrile, N-phenylaminoacetonitrile, N-(4-methylphenyl)aminoacetonitrile, N-methylaminopropionitrile, N-n-propylaminopropionitrile, N-isopropylaminopropionitrile, N-n-butylaminopropionitrile, N-isobutylaminopropionitrile, N-sec-butylaminopropionitrile, N-ocylaminopropionitrile, N-cyclohexylaminopropionitrile, methyl N-cyanomethylcarbamate, ethyl N-cyanomethylcarbamate, ethyl N-cyanoethylcarbamate, etc.

Representative examples of the amine compound of the formula (VIII) are methyl iminodiacetate, ethyl iminodiacetate, isopropyl iminodiacetate, butyl iminodiacetate, pentyl iminodiacetate, hexyl iminodiacetate, cyclopropyl iminodiacetate, cyclopentyl iminodiacetate, cyclohexyl iminodiacetate, methyl iminodipropionate, ethyl iminodipropionate, ethyl N-ethoxycarbonylmethylaminopropionate, ethyl 4-(ethoxycarbonylmethylamino)butyrate, ethyl-2-(ethoxycarbonylmethylamino)butyrate, etc.

Representative examples of the amine compound of the formula (IX) are N-cyanomethylglycine ethyl ester, N-cyanoethylglycine ethyl ester, ethyl N-cyanomethylaminopropionate, ethyl N-cyanoethylaminopropionate, etc.

Representative examples of the amine compound of the formula (X) are iminodiacetonitrile, iminodipropionitrile, iminodibutyronitrile, etc.

The aminosulfenyl chloride derivative of the formula (I) can be prepared in any of the above-described Methods 1 and 2. However, its preparation may be selected by the kind of the amine compound of the formula (IV). For example, when the amine compound is represented by the formula (VI) or (VII) wherein R represents Z'-R$^{4'}$, Method 2 is preferable. With respect to other amine compounds, there is no substantial difference between Method 1 and Method 2.

Typical of the compounds of the formula (I) are those as described in Examples 1 to 34 set forth hereinafter.

The reaction between the compound of the formula (I) and the compound of the formula (II) may be conducted in the presence or absence of a solvent. Examples of the solvent which can be used include halogenated hydrocarbons such as methylene chloride, chloroform, carbon tetrachloride, dichloroethane, trichloroethylene, methylchloroform, etc.; and ethers such as diethyl ether, dipropyl ether, dibutyl ether, tetrahydrofuran, dioxane, etc. The proportion of the compound of the formula (II) and the compound of the formula (I) is not particularly limited but is widely variable suitably. Usually, about 1 to about 2 moles, preferably 1 to 1.2 moles, of the latter is used per mole of the former. Preferably, the reaction is carried out in the presence of a basic compound. Examples of the basic compound which can be used include tertiary amines such as triethylamine, tributylamine, dimethylaniline, diethylaniline, ethylmorpholine, etc.; and pyridines such as pyridine, picoline, lutidine, etc. The basic compound can be used in an amount sufficient to capture the hydrogen chloride to be produced by the reaction as a by-product. Usually, about 1 to about 10 moles, preferably 1 to 5 moles, of the basic compound is used per mole of the compound of the formula (II). The reaction, which proceeds with cooling, at room temperature or with heating, is carried out usually at about −20° to about 50° C., preferably 0° to 40° C. The reaction time varies depending upon the kind and amount of the basic compound used, etc., but usually is about 1 to about 20 hours.

The compound of the formula (III) thus-obtained can be easily isolated and purified by a usual method of separation, such as solvent extraction, recrystallization or column chromatography.

Typical of the compounds of the formula (III) are those as described in Examples 35 to 42 set forth hereinafter.

The compounds of the formula (III) have outstanding insecticidal activity or controlling effect on agricultural and forestry noxious insects and household noxious insects and are comparable in such effect to carbonfuran which has the highest insecticidal activity heretofore known. These compounds are effective on a wide variety of noxious insects, mites and nematodes which are harmful to vegetables, trees, other plants and man, such as Hemiptera, Lepidoptera, Coleoptera, Diptera, Thysanoptera, Orthoptera, Isopoda, Acarina, Tylenchida, etc.

The toxicity of the compounds of the formula (III) to warm-blooded animals is as low as about 1/5 to about 1/100 the toxicity of carbofuran. These compounds exhibit insecticidal activity or controlling effect on the above-mentioned organisms in any stage or a specific stage of their growth and are therefore effectively usable for controlling them in the fields or agriculture, forestry and sanitation.

In practical uses, the compounds of the formula (III) are formulated into various forms, such as an emulsion, wettable powder, suspension, concentrated suspension, granule, fine particle, pellet, dust, coating composition, foam spray, aerosol, microcapsule composition, impregnant to be applied to a natural or synthetic material, fumigant, concentrated preparation to be applied in a small amount, etc.

The following Examples 1 to 34 will explain in greater detail the preparation of the compound of the formula (I).

EXAMPLE 1

Preparation of Bis(ethoxycarbonylmethyl)aminosulfenyl Chloride 2.1 g (0.02 mole) of sulfur dichloride was dissolved in 35 ml of carbon tetrachloride, and 1.6 g (0.02 mole) of pyridine was dropwise added to the resulting solution at 0° to 5° C. After completion of the dropwise addition, 3.8 g (0.02 mole) of ethyl iminodiacetate was further dropwise added thereto at 10° to 20° C., and the resulting mixture was stirred for one hour at the same temperature. After completion of the reaction, crystals were filtered off, and the mother liquor was concentrated under reduced pressure to obtain an oily product. Yield: 5.0 g (98%).

The NMR in CDCl$_3$ of this oily product is as follows: δ1.28 ppm (t, 6H), δ4.18 ppm (q, 4H), δ4.28 ppm (s, 4H).

The IR absorption spectrum showed absorption peaks at 1750 cm$^{-1}$ for

and 765 cm$^{-1}$ for —S—Cl, respectively.

Thus, the product was confirmed to have the following formula:

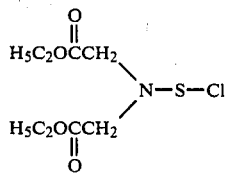

EXAMPLE 2

Preparation of Bis(ethoxycarbonylmethyl)aminosulfenyl Chloride 2.7 g (0.02 mole) of sulfur monochloride was dissolved in 35 ml of methylene chloride, and 1.6 g (0.02 mole) of pyridine was dropwise added to the resulting solution at 0° to 5° C. After completion of the dropwise addition, 3.8 g (0.02 mole) of ethyl iminodiacetate was further dropwise added thereto at 10° to 20° C., and the resulting mixture was stirred for one hour at the same temperature. After completion of the reaction, crystals were filtered off, and the mother liquor was concentrated under reduced pressure to obtain an oily product. Yield: 4.9 g (96%).

This oily product was the same as that obtained in Example 1.

EXAMPLE 3

Preparation of Bis(isopropoxycarbonylmethyl)aminosulfenyl Chloride 2.1 g (0.02 mole) of sulfur dichloride was dissolved in 35 ml of carbon tetrachloride, and 1.6 g (0.02 mole) of pyridine was dropwise added to the resulting solution at 0° to 5° C. After completion of the dropwise addition, 4.3 g (0.02 mole) of isopropyl iminodiacetate was further dropwise added thereto at 10° to 20° C., and the resulting mixture was stirred for one hour at the same temperature. After completion of the reaction, crystals were filtered off, and the mother liquor was concentrated under reduced pressure to obtain an oily product. Yield: 5.5 g (97%).

The NMR in CDCl$_3$ of this oily product is as follows: δ1.26 ppm (d, 12H), δ4.20 ppm (s, 4H), δ5.09 ppm (m, 2H).

The IR absorption spectrum showed absorption peaks at 1745 cm$^{-1}$ for

and 770 cm$^{-1}$ for —S—Cl, respectively.

Thus, the product was confirmed to have the following formula:

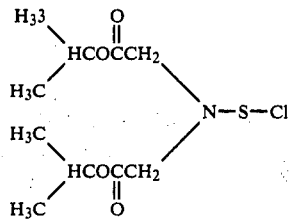

EXAMPLE 4

Preparation of Bis(methoxycarbonylmethyl)aminosulfenyl Chloride

The same procedure as in Example 1 was repeated except that methyl iminodiacetate was used in place of ethyl iminodiacetate. Thus, the titled compound in an oily state was obtained.

The NMR in CDCl$_3$ of this compound is as follows: δ3.78 ppm (s, 6H), δ4.29 ppm (s, 4H).

EXAMPLE 5

Preparation of Bis(cyclohexyloxycarbonylmethyl)aminosulfenyl Chloride

The same procedure as in Example 1 was repeated except that cyclohexyl iminodiacetate was used in place of ethyl iminodiacetate. Thus, the titled compound in an oily state was obtained.

The NMR in CDCl$_3$ of this compound is as follows: δ1.0–2.2 ppm (m, 20H), δ4.25 ppm (s, 4H), δ4.6–5.2 ppm (m, 2H).

EXAMPLE 6

Preparation of
N-Acetyl-N-ethoxycarbonylmethylaminosulfenyl
Chloride 2.7 g (0.02 mole) of their monochloride was dissolved in 50 ml of carbon tetrachloride, and 2.9 g (0.02 mole) of N-acetylglycine ethyl ester was dropwise added to the resulting solution at 0° to 5° C. After completion of the dropwise addition, 2.4 g (0.024 mole) of triethylamine was further dropwise added thereto at the same temperature, and the resulting mixture was stirred for one hour at the same temperature. After completion of the reaction, crystals were filtered off, and the mother liquor was concentrated under reduced pressure to obtain an oily product. Yield: 3.8 g (90.5%).

The NMR in CDCl$_3$ of this oily product is as follows:
$\delta$1.24 ppm (t, 3H), $\delta$2.52 pm (s, 3H), $\delta$4.14 ppm (q, 4H), $\delta$4.38 ppm (s, 2H).

Thus, this oily product was confirmed to have the following formula:

$$Cl-S-N\begin{matrix}CH_2COOC_2H_5\\COCH_3\end{matrix}$$

EXAMPLE 7

Preparation of
N-Methoxycarbonyl-N-ethoxycarbonylmethylaminosulfenyl Chloride 2.1 g (0.02 mole) of sulfur dichloride was dissolved in 50 ml of carbon tetrachloride, and 1.6 g (0.02 mole) of pyridine was dropwise added to the resulting solution at 0° to 5° C. After completion of the dropwise addition, 3.2 g (0.02 mole) of N-glycine ethyl ester was further dropwise added thereto at 10° to 20° C., and the resulting mixture was stirred for one hour at the same temperature. After completion of the reaction, crystals were filtered off, and the mother liquor was concentrated under reduced pressure to obtain an oily product. Yield: 4.2 g (93.3%).

The NMR in CDCl$_3$ of this oily product is as follows:
$\delta$1.27 ppm (t, 3H), $\delta$3.79 ppm (s, 3H), $\delta$4.16 ppm (q, 2H), $\delta$4.35 ppm (s, 2H).

The NMR analysis showed that the oily product contained small amounts of the starting materials and bisaminosulfide, but confirmed it to have the following formula:

$$Cl-S-N\begin{matrix}CH_2COOC_2H_5\\COOCH_3\end{matrix}$$

EXAMPLE 8

Preparation of
N-n-Butyl-N-ethoxycarbonylethylaminosulfenyl
Chloride 1.4 g (0.01 mole) of sulfur monochloride was dissolved in 50 ml of carbon tetrachloride, and to the resulting solution were dropwise added successively 3.5 g (0.02 mole) of ethyl N-butylaminopropionate and 2 g (0.02 mole) of triethylamine at 0° to 5° C. After completion of the dropwise addition, the resulting mixture was stirred for one hour, and the reaction solution was washed with 50 ml of water three times. The carbon tetrachloride layer was dried over sodium sulfate and subjected to filtration, and the carbon tetrachloride solution was again cooled to 0° C. with stirring. After the cooling, 1.4 g (0.01 mole) of sulfuryl chloride was dropwise added thereto under cooling and stirred for one hour at the same temperature. The reaction solution was concentrated under reduced pressure to obtain an oily product. Yield: 4.5 g (93.8%).

The NMR in CDCl$_3$ of this oily product is as follows:
$\delta$0.7-2.0 ppm (m, 7H), $\delta$1.26 ppm (t, 3H), $\delta$2.70 ppm (t, 2H), $\delta$3.25 ppm (t, 2H), $\delta$3.43 ppm (t, 2H), $\delta$4.08 ppm (q, 2H).

The NMR analysis showed that this ouly product contained a small amount of bisaminodisulfide, but confirmed it to have the following formula:

$$Cl-S-N\begin{matrix}CH_2CH_2COOC_2H_5\\CH_2CH_2CH_2CH_3\end{matrix}$$

EXAMPLE 9

Preparation of
N-Isopropyl-N-ethoxycarbonylethylaminosulfenyl
Chloride 3.2 g (0.02 mole) of ethyl N-isopropylaminopropionate was dissolved in 30 ml of n-hexane, and 50 ml of a 5% sodium hydroxide aqueous solution was added thereto. After cooling the mixture to 5° C., a solution of 1.4 g (0.01 mole) of sulfur monochloride dissolved in 50 ml of n-hexane was dropwise added thereto, and the resulting solution was stirred for one hour at the same temperature. After completion of the reaction, the n-hexane layer was separated, washed with water, and then dried. The n-hexane layer was again stirred under cooling, and 1.4 g (0.01 mole) of sulfuryl chloride was dropwise added thereto, followed by stirring for one hour. The n-hexane was concentrated under reduced pressure to obtain an oily product. Yield: 4.1 g (91%).

The NMR in CDCl$_3$ of this oily product is as follows:
$\delta$1.23 ppm (t, 3H), $\delta$1.26 ppm (d, 6H), $\delta$2.77 ppm (t, 2H), $\delta$3.0-3.8 ppm (m, 3H), $\delta$4.06 ppm (q, 2H).

The NMR analysis showed that this oily product contained a small amount of bisaminodisulfide, but confirmed it to have the following formula:

$$Cl-S-N\begin{matrix}CH_2CH_2COOC_2H_5\\CH\begin{matrix}CH_3\\CH_3\end{matrix}\end{matrix}$$

EXAMPLES 10 TO 34

The compounds shown in Table 1 below were prepared in the same manner as in Examples 6 to 9. The NMR data (in CDCl$_3$) of these compounds are also shown in Table 1.

TABLE 1

| Example No. | Structure | NMR (in CDCl$_3$) ppm |
|---|---|---|
| 10 | Cl—S—N(CH$_2$COOC$_2$H$_5$)(CH$_2$CH$_2$CH$_2$CH$_3$) | δ 0.7–2.0 (m, 7H), δ 1.29 (t, 3H), δ 3.31 (t, 2H), δ 4.05 (s, 2H), δ 4.16 (q, 2H) |
| 11 | Cl—S—N(CH$_2$COOC$_2$H$_5$)(3-CH$_3$-C$_6$H$_4$) | δ 1.26 (t, 3H), δ 2.34 (s, 3H), δ 4.13 (q, 2H), δ 4.59 (s, 2H), δ 6.9–7.5 (m, 4H) |
| 12 | Cl—S—N(CH$_2$COOC$_2$H$_5$)(C$_6$H$_4$-OCH$_3$) | δ 1.18 (t, 3H), δ 3.67 (s, 3H), δ 4.08 (q, 2H), δ 4.46 (s, 2H), δ 6.9–7.5 (m, 4H) |
| 13 | Cl—S—N(CH$_2$COOC$_2$H$_5$)(COCH$_2$CH$_3$) | δ 1.19 (t, 3H), δ 1.29 (t, 3H), δ 2.96 (t, 2H), δ 4.23 (q, 2H), δ 4.39 (s, 2H) |
| 14 | Cl—S—N(CH$_2$COOC$_2$H$_5$)(CO-C$_6$H$_5$) | δ 1.29 (t, 3H), δ 4.19 (q, 2H), δ 4.53 (s, 2H), δ 7.1–7.8 (m, 5H) |
| 15 | Cl—S—N(CH$_2$COOC$_2$H$_5$)(SO$_2$-C$_6$H$_4$-CH$_3$) | δ 1.26 (t, 3H), δ 2.45 (s, 3H), δ 4.16 (q, 2H), δ 4.38 (s, 2H), δ 7.2–8.0 (m, 4H) |
| 16 | Cl—S—N(CH$_2$COOC$_2$H$_5$)(COOCH$_3$) | δ 1.28 (t, 3H), δ 3.81 (s, 3H), δ 4.17 (q, 2H), δ 4.36 (s, 2H) |
| 17 | Cl—S—N(CH$_2$COOC$_2$H$_5$)(COOC$_2$H$_5$) | δ 1.27 (t, 3H), δ 1.33 (t, 3H), δ 4.16 (q, 2H), δ 4.25 (q, 2H), δ 4.39 (s, 2H) |
| 18 | Cl—S—N(CH$_2$COOC$_2$H$_5$)(COO-C$_6$H$_5$) | δ 1.30 (t, 3H), δ 4.15 (q, 2H), δ 4.48 (s, 2H), δ 6.9–7.6 (m, 5H) |
| 19 | Cl—S—N(CH$_2$COOC$_2$H$_5$)(CH$_2$CH$_2$CN) | δ 1.30 (t, 3H), δ 2.89 (t, 2H), δ 3.65 (t, 2H), δ 4.20 (s, 2H), δ 4.26 (q, 2H) |
| 20 | Cl—S—N(CH$_2$CN)(CH(CH$_3$)$_2$) | δ 1.33 (d, 6H), δ 3.3–3.9 (m, 1H), δ 4.32 (s, 2H) |
| 21 | Cl—S—N(CH$_2$CN)(CH$_2$CH$_2$CH$_2$CH$_3$) | δ 0.7–2.0 (m, 7H), δ 3.22 (t, 2H), δ 4.05 (s, 2H) |
| 22 | Cl—S—N(CH$_2$CH$_2$COOC$_2$H$_5$)(CH$_2$CH$_2$CH$_3$) | δ 0.93 (t, 3H), δ 1.24 (t, 3H), δ 1.4–2.2 (m, 2H), δ 2.68 (t, 2H), δ 3.20 (t, 2H), δ 3.43 (t, 2H), δ 4.06 (q, 2H) |

TABLE 1-continued

| Example No. | Structure | NMR (in CDCl$_3$) ppm |
|---|---|---|
| 23 | Cl—S—N(CH$_2$CH$_2$COOC$_2$H$_5$)(CH(CH$_3$)CH$_3$) | δ 1.23 (t, 3H), δ 1.26 (d, 6H), δ 2.77 (t, 2H), δ 3.0–3.8 (m, 3H), δ 4.06 (q, 2H) |
| 24 | Cl—S—N(CH$_2$CH$_2$COOCH$_3$)(CH$_2$CH$_2$CH$_2$CH$_3$) | δ 0.7–2.0 (m, 7H), δ 2.62 (t, 2H), δ 3.17 (t, 2H), δ 3.36 (t, 2H), δ 3.58 (s, 3H) |
| 25 | Cl—S—N(CH$_2$CH$_2$COOC$_2$H$_5$)(CH$_2$CH(CH$_3$)CH$_3$) | δ 0.87 (d, 6H), δ 1.34 (t, 3H), δ 1.6–2.2 (m, 1H), δ 2.74 (t, 2H), δ 4.13 (q, 2H), δ 2.95–3.6 (m, 4H) |
| 26 | Cl—S—N(CH$_2$CH$_2$COOC$_2$H$_5$)(C(CH$_3$)$_3$) | δ 1.26 (t, 3H), δ 1.39 (s, 9H), δ 2.76 (t, 2H), δ 3.53 (t, 2H), δ 4.14 (q, 2H) |
| 27 | Cl—S—N(CH$_2$CH$_2$COOC$_2$H$_5$)(CH$_2$CH$_2$CH$_2$CH$_2$CH$_2$CH$_3$) | δ 0.6–2.0 (m, 14H), δ 2.62 (t, 2H), δ 3.19 (t, 2H), δ 3.39 (t, 2H), δ 4.02 (q, 2H) |
| 28 | Cl—S—N(CH$_2$CH$_2$COOC$_2$H$_5$)(cyclohexyl-H) | δ 0.8–2.2 (m, 10H), δ 1.24 (t, 3H), δ 2.65 (t, 2H), δ 2.8–3.5 (m, 3H), δ 4.06 (q, 2H) |
| 29 | Cl—S—N(CH$_2$CH$_2$CN)(CH$_2$CH(CH$_3$)CH$_3$) | δ 0.91 (d, 6H), δ 1.7–2.5 (m, 1H), δ 2.5–3.2 (m, 4H), δ 3.39 (t, 2H) |
| 30 | Cl—S—N(CH$_2$CH$_2$CN)(C(CH$_3$)$_3$) | δ 1.35 (s, 9H), δ 2.85 (t, 2H), δ 3.57 (t, 2H) |
| 31 | Cl—S—N(CH$_2$CH$_2$CN)(CH$_2$CH$_2$CN) | δ 2.94 (t, 4H), δ 3.68 (t, 4H) |
| 32 | Cl—S—N(CH$_2$CH$_2$COOC$_2$H$_5$)(CH$_2$—C$_6$H$_5$) | δ 1.26 (t, 3H), δ 2.75 (t, 2H), δ 3.35 (t, 2H), δ 3.94 (s, 2H), δ 4.16 (q, 2H), δ 6.9–7.5 (m, 5H) |
| 33 | Cl—S—N(CH$_2$CH$_2$COOC$_2$H$_5$)(CH$_2$—C$_6$H$_4$—Cl) | δ 1.24 (t, 3H), δ 2.74 (t, 2H), δ 3.33 (t, 2H), δ 4.01 (s, 2H), δ 4.14 (q, 2H), δ 7.0–7.8 (m, 4H) |
| 34 | Cl—S—N(CH$_2$CH$_2$COOC$_2$H$_5$)(C$_6$H$_5$) | δ 1.24 (t, 3H), δ 2.73 (t, 2H), δ 3.35 (t, 2H), δ 4.11 (q, 2H), δ 7.0–7.5 (m, 5H) |

The following Examples 35 to 42 will explain in greater detail the preparation of the compound of the formula (III).

EXAMPLE 35

Preparation of 2,3-Dihydro-2,2-dimethylbenzofuran-7-yl N-[N,N-Bis(ethoxycarbonylmethyl)aminosulfenyl]-N-methylcarbamate 4.4 g (0.02 mole) of 2,3-dihydro-2,2-dimethylbenzofuran-7-yl N-methyl-carbamate, 5.1 g (0.02 mole) of bis(ethoxycarbonylmethyl)aminosulfenyl chloride obtained in Example 1 or 2, and 4.7 g (0.06 mole) of pyridine were dissolved in 35 ml of methylene chloride, and the resulting solution was stirred for 30 hours at 30° to 35° C. After completion of the reaction, the reaction solution was washed successively with water, diluted hydrochloric acid and water. The methylene chloride layer was dried over sodium sulfate and concentrated under reduced pressure to obtain an oily product. Yield: 7.5 g (85.2%).

For the identification of the product, a portion thereof was purified by silica gel column chromatography, using benzene/ethyl acetate (4:1) as the elution solvent, whereby an oily product was obtained.

NMR in CDCl$_3$: δ 1.24 ppm (t, 6H), δ 1.48 ppm (s, 6H), δ 3.02 ppm (s, 2H), δ 3.42 ppm (s, 3H), δ 4.20 ppm (q, 4H), δ 4.28 ppm (s, 4H), δ 6.6.–7.2 ppm (m, 3H).

Elemental Analysis:

|  | C | H | N |
| --- | --- | --- | --- |
| Found (%) | 54.49 | 6.47 | 6.40 |
| Calcd. for C$_{20}$H$_{28}$N$_2$O$_7$S (molecular wt. 440.53) | 54.53 | 6.41 | 6.36 |

Thus, the product was confirmed to have the following formula:

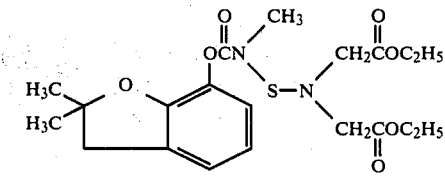

EXAMPLE 36

Preparation of 2,3-Dihydro-2,2-dimethylbenzofuran-7-yl N-[N,N-Bis(isopropoxycarbonylmethyl)aminosulfenyl]-N-methyl-carbamate 4.4 g (0.02 mole) of 2,3-dihydro-2,2-dimethylbenzofuran-7-yl N-methyl carbamate, 5.7 g (0.02 mole) of bis(isopropoxycarbonylmethyl)aminosulfenyl chloride obtained in Example 3, and 4.7 g (0.06 mole) of pyridine were dissolved in 30 ml of chloroform, and the resulting solution was stirred for 30 hours at 30° C. After completion of the reaction, the reaction solution was washed successively with water, diluted hydrochloric acid and water. The chloroform layer was dried over sodium sulfate and concentrated under reduced pressure to obtain an oily product which was almost entirely composed of the desired product although containing small amounts of the starting materials and impurities. Yield: 7.9 g (84.0%).

For the identification of the product, a portion thereof was purified by silica gel column chromatography, using benzene/ethyl acetate (4:1) as the elution solvent, whereby an oily product was obtained.

NMR in CDCl$_3$: δ 1.23 ppm (d, 6H), δ 1.46 ppm (s, 6H), δ 3.03 ppm (s, 2H), δ 3.42 ppm (s, 3H), δ 4.26 ppm (s, 4H), δ 5.08 ppm (m, 1H), δ 6.6–7.2 ppm (m, 3H).

Elemental Analysis:

|  | C | H | N |
| --- | --- | --- | --- |
| Found (%) | 56.35 | 6.91 | 5.86 |
| Calcd. for C$_{22}$H$_{32}$N$_2$O$_7$S (molecular wt. 468.49) | 56.40 | 6.89 | 5.98 |

Thus, the product was confirmed to have the following formula:

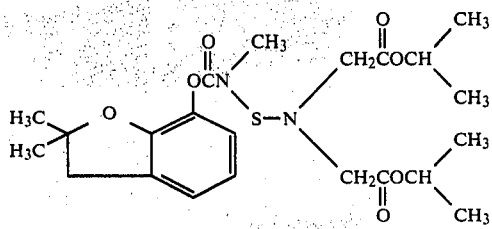

EXAMPLE 37

Preparation of 2,3-Dihydro-2,2-dimethylbenzofuran-7-yl N-[N,N-Bis(methoxycarbonylmethyl)aminosulfenyl]-N-methylcarbamate The same procedure as in Example 35 was repeated except that bis(methoxycarbonylmethyl)aminosulfenyl chloride as obtained in Example 4 was used in place of bis(ethoxycarbonylmethyl)aminosulfenyl chloride. Thus, an oily product was obtained.

NMR in CDCl$_3$: δ 1.47 ppm (s, 6H), δ 3.02 ppm (s, 2H), δ 3.41 ppm (s, 3H), δ 3.73 ppm (s, 6H), δ 4.30 ppm (s, 4H), δ 6.7–7.2 ppm (m, 3H).

Elemental Analysis:

|  | C | H | N |
| --- | --- | --- | --- |
| Found (%) | 52.11 | 5.91 | 6.63 |
| Calcd. for C$_{18}$H$_{24}$N$_2$O$_7$S (molecular wt. 412.47) | 52.42 | 5.87 | 6.79 |

Thus, the product was confirmed to have the following formula:

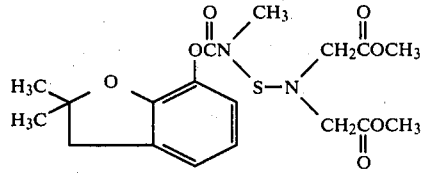

EXAMPLE 38

Preparation of 2,3-Dihydro-2,2-dimethylbenzofuran-7-yl N-[N,N-Bis(cyclohexyloxycarbonylmethyl)aminosulfenyl]-N-methyl-carbamate The same procedure as in Example 35 was repeated except that bis(cyclohexyloxycarbonylmethyl)aminosulfenyl chloride as obtained in Example 5 was used in place of bis(ethoxycarbonylmethyl)aminosulfenyl chloride. Thus, an oily product was obtained.

NMR in CDCl$_3$: δ 1.0–2.2 ppm (m, 20H), δ 1.48 ppm (s, 6H), δ 3.02 ppm (s, 2H), δ 3.43 ppm (s, 3H), δ 4.28 ppm (s, 4H), δ 4.5–5.1 ppm (m, 2H), δ 6.7–7.2 ppm (m, 3H).

Elemental Analysis:

|  | C | H | N |
|---|---|---|---|
| Found (%) | 61.32 | 7.39 | 4.95 |
| Calcd. for C$_{28}$H$_{40}$N$_2$O$_7$S (molecular wt. 548.71) | 61.29 | 7.35 | 5.11 |

Thus, the product was confirmed to have the following formula:

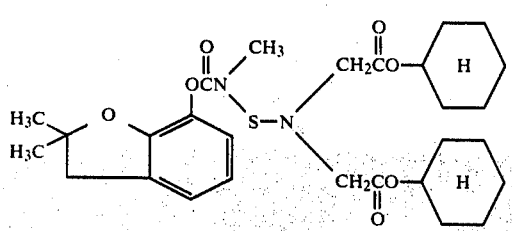

EXAMPLE 39

Preparation of 2,3-Dihydro-2,2-dimethylbenzofuran-7-yl N-[N,N-Bis(cyanoethyl)aminosulfenyl]-N-methyl-carbamate 4.4 g (0.02 mole) of 2,3-dihydro-2,2-dimethylbenzofuran-7-yl N-methyl-carbamate, 3.8 g (0.02 mole) of bis(cyanoethyl)aminosulfenyl chloride obtained in Example 31, and 4.7 g (0.06 mole) of pyridine were dissolved in 35 ml of methylene chloride, and the resulting solution was stirred for 20 hours at 25° to 30° C. After completion of the reaction, the reaction solution was washed successively with water, diluted hydrochloric acid and water. The methylene chloride layer was dried over sodium sulfate and concentrated under reduced pressure to obtain an oily product which was almost entirely composed of the desired product although containing small amounts of the starting materials and impurities. Yield: 6.2 g (82.7%).

For the identification of the product, a portion thereof was purified by silica gel column chromatography, using benzene/ethyl acetate (4:1) as the elution solvent, whereby an oily product was obtained.

NMR in CDCl$_3$: δ 1.43 ppm (s, 6H), δ 2.73 ppm (t, 4H), δ 2.97 ppm (s, 2H), δ 3.37 ppm (s, 3H), δ 3.43 ppm (t, 4H), δ 6.5–7.2 ppm (m, 3H).

Elemental Analysis:

|  | C | H | N |
|---|---|---|---|
| Found (%) | 57.84 | 5.81 | 15.06 |
| Calcd. for C$_{18}$H$_{22}$N$_4$O$_3$S (molecular wt. 374.472) | 57.73 | 5.92 | 14.96 |

Thus, the product was confirmed to have the following formula:

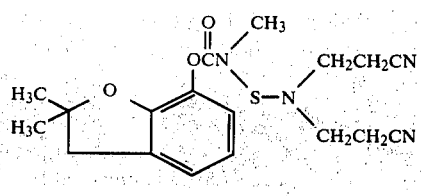

EXAMPLE 40

Preparation of 2,3-Dihydro-2,2-dimethylbenzofuran-7-yl N-(N-n-Butyl-N-ethoxycarbonylethylaminosulfenyl)-N-methyl-carbamate 2.2 g (0.01 mole) of 2,3-dihydro-2,2-dimethylbenzofuran-7-yl N-methyl-carbamate and 2.4 g (0.01 mole) of N-n-butyl-N-ethoxycarbonylethylaminosulfenyl chloride as obtained in Example 8 were dissolved in 30 ml of methylene chloride, and the solution was cooled to 0° C. 1.2 g (0.012 mole) of triethylamine was dropwise added thereto with stirring, and allowed to react for 2 hours at the same temperature. After completion of the reaction, the reaction solution was washed successively with water, diluted hydrochloric acid and water. The methylene chloride layer was dried and concentrated under reduced pressure to obtain an oily product which was almost entirely composed of the desired product although containing small amounts of the starting materials and impurities.

For the identification of the product, a portion thereof was purified by silica gel column chromatography, using benzene/ethyl acetate (10:1) as the elution solvent, whereby an oily product was obtained.

NMR in CDCl$_3$: δ 0.7–1.8 ppm (m, 10H), δ 1.41 ppm (s, 6H), δ 2.4–2.8 ppm (m, 2H), δ 2.95 ppm (s, 2H), δ 3.33 ppm (s, 3H), δ 3.1–3.4 ppm (m, 4H), δ 3.97 ppm (q, 2H), δ 6.6–7.2 ppm (m, 3H).

Elemental Analysis:

|  | C | H | N |
|---|---|---|---|
| Found (%) | 59.01 | 7.38 | 6.79 |
| Calcd. for C$_{21}$H$_{32}$N$_2$O$_5$S (molecular wt. 424.569) | 59.42 | 7.60 | 6.60 |

Thus, the product was confirmed to have the following formula:

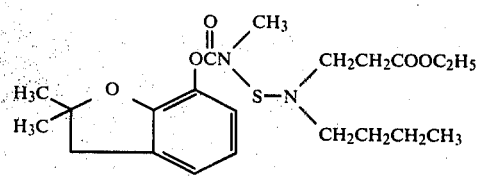

EXAMPLE 41

Preparation of 2,3-Dihydro-2,2-dimethylbenzofuran-7-yl N-(N-Isopropyl-N-cyanoethylaminosulfenyl)-N-methyl-carbamate 2.2 g (0.01 mole) of 2,3-dihydro-2,2-dimethylbenzofuran-7-yl N-methyl-carbamate and 1.8 g (0.01 mole) of N-isopropyl-N-cyanoethylaminosulfenyl chloride were dissolved in 30 ml of methylene chloride, and the solution was cooled to 0° C. 1.2 g (0.012 mole) of triethylamine was dropwise added thereto with stirring, and allowed to react for 2 hours at the same temperature. After completion of the reaction, the reaction solution was washed successively with water, diluted hydrochloric acid and water. The methylene chloride layer was dried and concentrated under reduced pressure to obtain an oily product which was almost entirely composed of the desired product although containing small amounts of the starting materials and impurities.

For the identification of the product, a portion thereof was purified by silica gel column chromatography, using benzene/ethyl acetate (10:1) as the elution solvent, whereby an oily product was obtained.

NMR in CDCl$_3$: δ 1.21 ppm (d, 6H), δ 1.43 ppm (s, 6H), δ 2.72 ppm (t, 2H), 67 3.00 ppm (s, 2H), δ 3.0–3.8 ppm (m, 3H), δ 3.32 ppm (s, 3H), δ 6.6–7.2 ppm (m, 3H).

Elemental Analysis:

|  | C | H | N |
|---|---|---|---|
| Found (%) | 59.55 | 6.74 | 11.84 |
| Calcd. for C$_{18}$H$_{25}$N$_3$O$_3$S (molecular wt. 363.488) | 59.49 | 6.93 | 11.56 |

Thus, the product was confirmed to have the following formula:

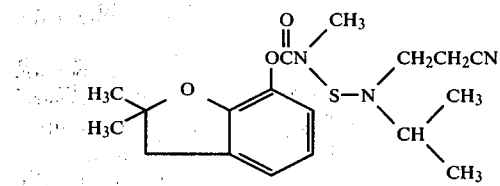

EXAMPLE 42

Preparation of 2,3-Dihydro-2,2-dimethylbenzofuran-7-yl N-(N-Ethoxycarbonyl-N-ethoxycarbonylmethylaminosulfenyl)-N-methyl-carbamate 2.2 g (0.01 mole) of 2,3-dihydro-2,2-dimethylbenzofuran-7-yl N-methyl-carbamate, 2.4 g (0.01 mole) of N-ethoxycarbonyl-N-ethoxycarbonylmethylaminosulfenyl chloride obtained in Example 17, and 3.2 g (0.04 mole) of pyridine were dissolved in 30 ml of chloroform, and the resulting solution was stirred for 24 hours at 20° to 30° C. After completion of the reaction, the reaction solution was washed successively with water, diluted hydrochloric acid and water. The chloroform layer was dried and concentrated under reduced pressure to obtain an oily product which was almost entirely composed of the desired product although containing small amounts of the starting materials and impurities.

For the identification of the product, a portion thereof was purified by silica gel column chromatography, using benzene/ethyl acetate (4:1) as the elution solvent, whereby an oily product was obtained.

NMR in CDCl$_3$: δ 1.17 ppm (t, 6H), δ 1.44 ppm (s, 6H), δ 2.94 ppm (s, 2H), δ 3.41 (s, 3H), δ 4.05 ppm (q, 2H), δ 4.15 ppm (q, 2H), δ 4.41 ppm (s, 2H), δ 6.5–7.0 ppm (m, 3H).

Elemental Analysis:

|  | C | H | N |
|---|---|---|---|
| Found (%) | 53.46 | 6.31 | 6.39 |
| Calcd. for C$_{19}$H$_{26}$N$_2$O$_7$S (molecular wt. 426.499) | 53.51 | 6.14 | 6.57 |

Thus, the product was confirmed to have the following formula:

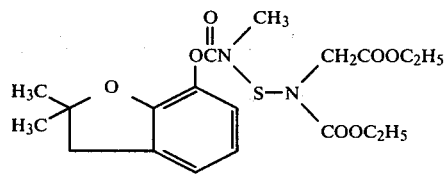

While the invention has been described in detail and with reference to specific embodiments thereof, it will be apparent to one skilled in the art that various changes and modifications can be made therein without departing from the spirit and scope thereof.

What is claimed is:

1. An aminosulfenyl chloride derivative represented by the formula (I):

wherein R$^1$ and R$^2$, which may be the same or different, each represents (1) —X—COOR$^3$, in which X represents an alkylene group having 1 to 6 carbon atoms, and R$^3$ represents an alkyl group having 1 to 8 carbon atoms or a cycloalkyl group having 3 to 6 carbon atoms; or (2) —Y—CN, in which Y represents an alkylene group having 1 to 6 carbon atoms; and R$^2$ further represents an alkyl group having 1 to 8 carbon atoms; a cycloalkyl group having 3 to 6 carbon atoms; a benzyl group which may be substituted with a halogen atom, an alkyl group having 1 to 3 carbon atoms or an alkoxy group having 1 to 3 carbon atoms; a phenyl group which may be substituted with a halogen atom, an alkyl group having 1 to 3 carbon atoms or an alkoxy group having 1 to 3 carbon atoms; or —Z—R$^4$, in which Z represents a carbonyl group or a sulfonyl group, and R$^4$ represents an alkyl group having 1 to 6 carbon atoms, a phenyl group which may be substituted with an alkyl group having 1 to 3 carbon atoms or a halogen atom, an alkoxy group having 1 to 3 carbon atoms or a phenoxy group.

* * * * *